(12) United States Patent
Schmidt et al.

(10) Patent No.: US 6,318,359 B1
(45) Date of Patent: Nov. 20, 2001

(54) HEAT PACK USING SUPER-COOLED AQUEOUS SALT SOLUTIONS

(76) Inventors: George Schmidt, 17 Morley Avenue, Brantford, Ontario (CA), N3S 7A7; Jeffrey Thomas Whitely, 151 Crestwood Court, Burlington, Ontario (CA), L7L 2V9

( * ) Notice: Subject to any disclaimer, the term of this patent is extended or adjusted under 35 U.S.C. 154(b) by 0 days.

(21) Appl. No.: 09/547,720

(22) Filed: Apr. 12, 2000

Related U.S. Application Data

(60) Provisional application No. 60/128,794, filed on Apr. 12, 1999.

(51) Int. Cl.[7] ............................................. F24J 1/00
(52) U.S. Cl. ................................ 126/263.03; 252/70
(58) Field of Search ...................... 126/263.01, 263.02, 126/263.03; 607/114; 252/70; 206/219

(56) References Cited

U.S. PATENT DOCUMENTS

| | | | |
|---|---|---|---|
| 1,385,074 | * | 7/1921 | Ferguson ..................... 126/263.03 |
| 1,920,853 | * | 8/1933 | Ferguson ..................... 126/263.03 |
| 3,951,127 | * | 4/1976 | Watson et al. ................ 126/263.03 |
| 4,057,047 | * | 11/1977 | Gossett ............................. 206/219 |
| 4,451,383 | * | 5/1984 | Arrhenius ..................... 126/263.03 |
| 4,834,802 | * | 5/1989 | Prier ................................. 607/114 |
| 4,856,651 | * | 8/1989 | Francis, Jr. ...................... 206/219 |
| 6,020,040 | * | 2/2000 | Cramer et al. ...................... 252/70 |
| 6,103,139 | * | 8/2000 | Kohout ........................ 126/263.03 |

* cited by examiner

Primary Examiner—Ira S. Lazarus
Assistant Examiner—Sara Clarke
(74) Attorney, Agent, or Firm—Dowell & Dowell, P.C.

(57) ABSTRACT

A heat pack containing a super-cooled aqueous solution is provided comprising a flexible container having at least two compartments separated by a rupturable seal housing an aqueous solution in one compartment and having the other compartment remain empty.

7 Claims, 5 Drawing Sheets

HEAT PACK USING SUPER-COOLED AQUEOUS SALT SOLUTIONS

CROSS REFERENCE TO RELATED APPLICATIONS

This application claims benefit of U.S. Provisional Application Serial No. 60/128,794, filed Apr. 12, 1999, entitled HEAT PACK USING SUPER-COOLED AQUEOUS SALT SOLUTION AND METHOD FOR MAKING SAME in the name of the same inventors.

BACKGROUND OF THE INVENTION

This invention relates to disposable heat packs for therapeutic use and more particularly to heat packs employing super-cooled aqueous salt solutions.

FIELD OF THE INVENTION

The use of disposable heat packs has grown considerably over the last several years. These heat packs offer an economical, safe and reliable way of applying heat for therapeutic use in both home and institutional settings. Disposable heat packs are often used at home for a number of ailments including to relieve pain caused from muscle strain or injury, or to relieve soreness. Certain specialized uses have also developed including relieving discomfort in the breast area in nursing mothers. Hospitals use disposable heat packs in a number of ways including to warm a newborn's heel prior to drawing blood, as is customary or required in many jurisdictions.

Heat packs can be both disposable and reusable and many types of both kinds are known. In institutional settings such as hospitals, disposable packs are preferred for ease of use and sanitary reasons. Typically such packs are used for only a few minutes and then discarded. An ideal disposable heat pack is both easy and quick to use, is completely safe and reliable, and is economical.

Disposable heat packs utilizing super-cooled aqueous salt solutions are well-known. These packs typically employ a flexible plastic container which houses the salt solution. The solution is "super-cooled" which means it is prepared in a very pure state and then heated to a high temperature. It is then cooled gradually to a temperature below its normal crystallization temperature. Normally the salt solution is prepared so that the super-cooled solution remains stable at ambient temperatures found in homes, hospitals and their related storage areas.

When the pack is to be used, crystallization in the solution is initiated. The latent heat of crystallization warms the pack as the solution turns from liquid to solid phase. If the correct formulation of salt solution is chosen, the phase change occurs at a constant temperature in a narrow range which is appropriate to warm human skin, The reaction is predictable and stable and lasts several minutes—enough for the pack to perform its task.

Much prior art exists teaching different container structures for the heat packs, and employing different salt solutions and different methods of initiating crystallization. In particular, much attention has been focused on various means or "triggers" to initiate crystallization of the solution.

U.S. Pat. No. 4,077,390 describes a flexible container filled with a super-cooled aqueous salt solution and also containing a flexible ferrous metal strip characterized by one or more fissures or slits which are said to initialize crystallization when the strip is flexed. The length, shape and location of the fissures and slits is carefully set out. The flexing is said to produce minute particles of metal around which crystallization occurs. Problems with this device can include breakage of the strip along a fissure which can render the device incapable of being triggered, or which can leave a sharp metal fragment in the container leading to rupture.

To overcome these problems, U.S. Pat. No. 4,460,546 (issued to the same patentee) teaches the use of pinhole openings in the metal strip in place of the fissures or slits. The material of the strip is amended from ferrous metal (or sometimes stainless steel) to a more exotic beryllium-copper alloy or phosphor-bronze. The problems with this trigger means include accidental triggering caused by routine handling and also the inability to trigger even after repeated attempts.

A third effort along these lines was made in U.S. Pat. No. 4,572,158. In this patent further refinement of the location, shape etc. of the slits is taught. This refinement is said to encourage minute "tearing" of the metal upon flexing, which exposes new metal to the solution and hence initiates crystallization. Again, repeated flexing can still fail to trigger this device in a significant number of units.

U.S. Pat. No. 4,872,442 (issued to a different patentee) is stated to solve these problems by providing a similar metal strip, additionally having eroded and roughened surfaces. The surface texture is said to enhance the separation of minute particles of metal upon flexing, which particles can then act as a nesting site for crystallization. Incidence of non-triggering units is said to be reduced. Manufacturing costs for these types of sophisticated triggering devices is high.

As early as 1933, in U.S. Pat. No. 1,915,523, it was taught that crystallization of a super-cooled aqueous solution of sodium acetate could be triggered by injecting the solution with air. A flexible container is provided with a semi-automatic valve that can be operated to allow air into the container thereby inducing crystal formation.

Recently, in U.S. Pat. No. 5,305,733, further attempts were made to trigger crystallization by introducing air into a container filled with super-cooled solution by building onto the container a metallic puncturing device. The puncturing device is attached to the outside of the container and is provided with prongs which are pushed through the container walls to allow air to enter and initiate crystallization. A sealing means has to be provided to prevent the solution from escaping the container once puncturing occurs. This device is stated to be an improvement over much earlier valve operated devices as triggering can be initiated with only one hand. Leakage after triggering is a problem that occurs with these devices. They must also be manufactured and handled carefully to avoid accidental triggering.

Attempts have also been made to employ chemical as opposed to mechanical triggering devices. Typically these devices are chemical-specific and not always adaptable for solutions with optimum properties.

U.S. Pat. No. 3,951,127 teaches triggering of a super-cooled salt solution, such as a sodium thiosulfate pentahydrate or a sodium acetate trihydrate solution, by introduction of a second chemical, being either sodium borate pentahydrate or sodium sulfite. The second chemical can be in crystal or solution form. The second chemical in solution form can be introduced to the first chemical through a valve arrangement. Alternatively, the second chemical, provided in crystal form, can be located in an outer container disposed around an inner container holding the first chemical in solution, and into which the first container is ruptured, thereby mixing the two chemicals. Problems with this arrangement include the properties of chemicals themselves, being both toxic to humans and also reacting at a higher than ideal temperature. To offset this the patent further teaches use of insulation to prevent excessive heat transfer to the person. Excessive heat can cause burning and in many jurisdictions non food-grade (toxic) chemicals are prohibited in institutional use.

It is an object of this invention to provide a disposable heat pack that is both easy and quick to use, is completely safe and reliable, and is economical. It is a further object of this invention to provide a heat pack devoid of ancillary mechanical or chemical triggering means, thus reducing the cost and complexity of manufacture.

SUMMARY OF THIS INVENTION

Thus there is provided a disposable heat pack using a food grade (non-toxic) aqueous salt solution hermetically sealed in a flexible container, with which air can be mixed by applying simple mechanical pressure with one hand to the exterior of the heat pack. Triggering requires no second chemicals, no metal or plastic disk or strip triggering means, and does not require puncturing of the pack in such a way as to ever allow the solution to escape outside the pack.

One embodiment of the pack uses a container with an interior baffle, or flangible seal, to create two separate compartments. One compartment houses the super-cooled solution and the other compartment houses just air. Upon applying firm but modest pressure the baffle, or seal, can be ruptured causing triggering.

Another embodiment utilizes a dual container system, having inner and outer hermetically sealed containers. The solution may be stored in either the inner or outer container with air being in the other container. The inner, but not the outer container is fabricated to be rupturable upon application of modest pressure, causing the solution to be exposed to the air, which in turn causes crystallization.

An attachment means, such as an adhesive strip, may be affixed to the pack to permit it to be secured to a person. The size and configuration of the pack may be altered to suit different applications such as for use as a breast pack or as an infant heel warmer.

BRIEF DESCRIPTION OF THE DRAWINGS

In order that the invention may be more clearly understood, one preferred embodiment thereof will now be described in detail by way of example, with reference to the accompanying drawings, in which.

DETAILED DESCRIPTION OF ONE PREFERRED EMBODIMENT

Figure 1:
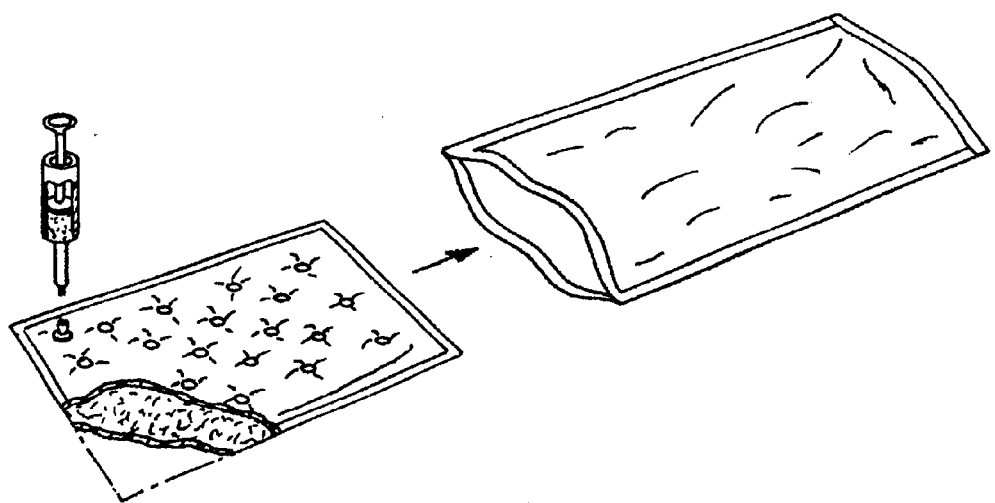
FIG. 1 is a prior art device using a valve and air injection triggering system.
Figure 2:
FIG. 2 is a prior art disk with a roughened surface used in a disk triggering system.
Figure 3:
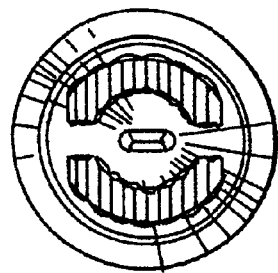
FIG. 3 is a prior art disk shown in top view with slits and holes, also used in a disk triggering system.
Figure 4:
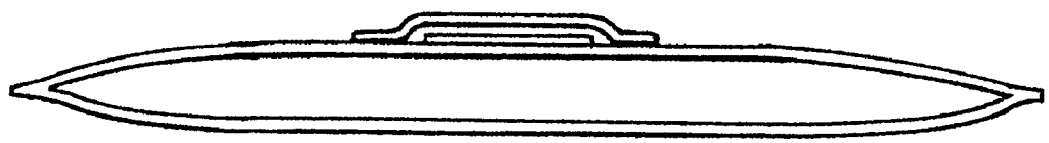
FIG. 4 is a prior art device using a puncturing system.
Figure 5:
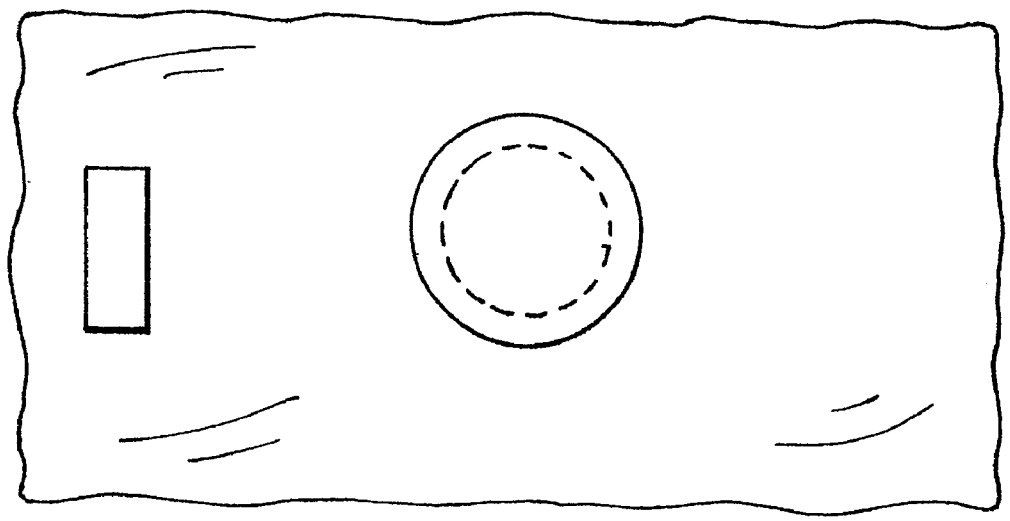
FIG. 5 is a top view of the prior art device of FIG. 4.
Figure 6:
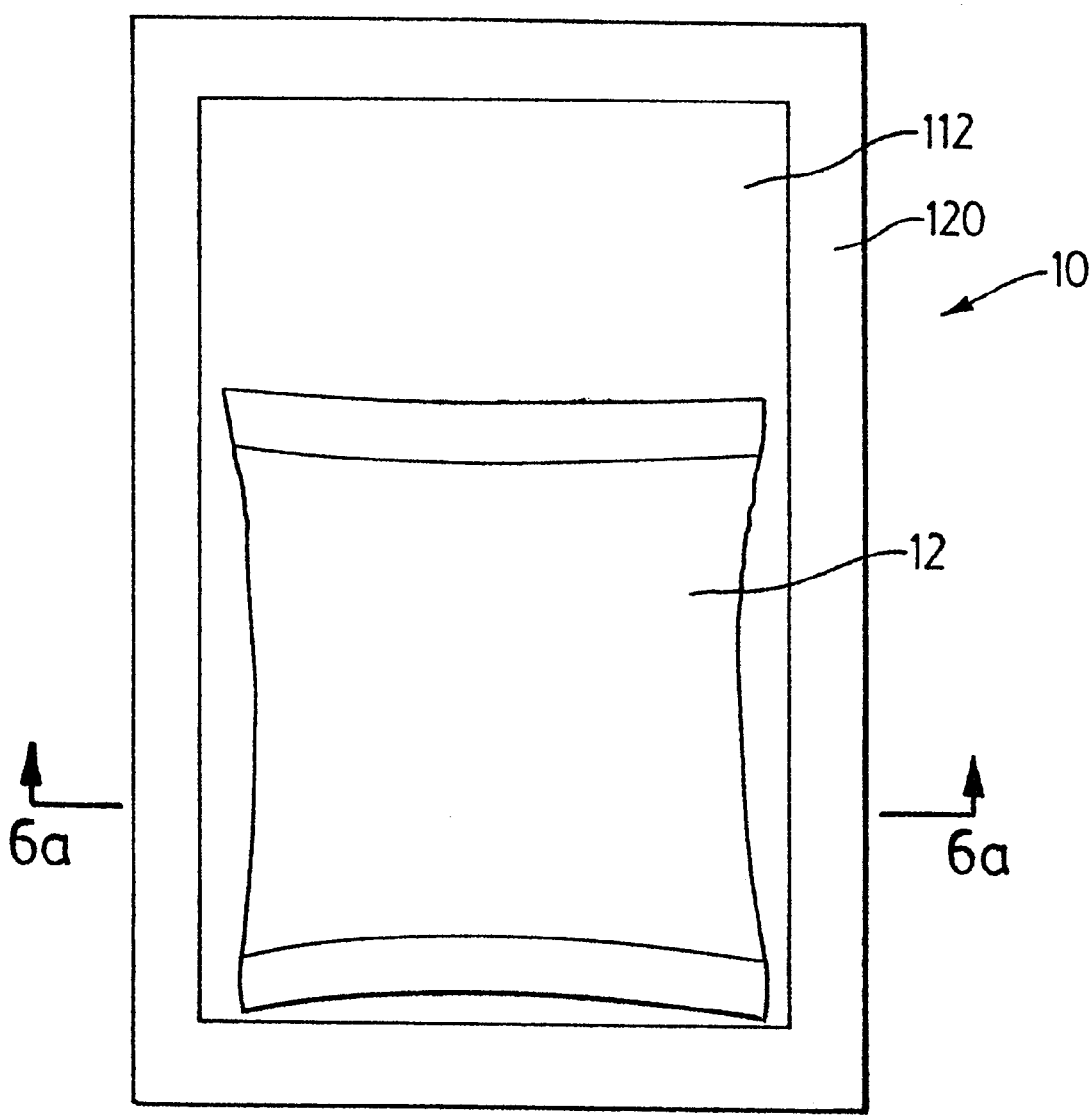
FIG. 6 is a top view of one embodiment of the present invention showing the solution in an inner container in a dual container system.
Figure 6A:
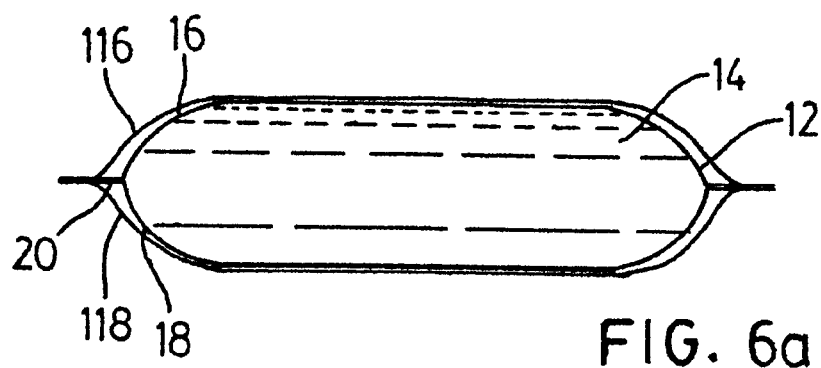
FIG. 6A is a sectional view along line 6A—6A of FIG. 6.

Referring now to the drawings, the parts identified will be referenced with the corresponding part numbers as shown in the following list:

Referring now to FIGS. 6, 6A, 7, 7A and 8, one embodiment of the present invention is shown to include a heat pack 10 with an inner container 12 and an outer container 112. The inner container has a first piece of sheet material 16 and a second piece of sheet material 18 both of generally rectangular shape and of approximately the same size and configuration, which first and second sheets are hermetically sealed at their edges to form the edges of the inner container 20.

The outer container 112 has a first piece of sheet material 116 and a second piece of sheet material 118 both of generally rectangular shape and of approximately the same size and configuration, which first and second sheets are hermetically sealed at their edges to form the edges of the outer container 120. The outer container 112 completely surrounds and encapsulates inner container 12.

The sheet material should be heat sealable to facilitate fabrication of the pack 10. Many suitable materials exist including polyesters and polynylons. One particularly suitable heat sealable plastic material is polyethylene. Polyethylene is low to medium density and is not expensive, and is easily heat sealed over a wide temperature range. Polyethylene sheet material is very flexible and will readily elongate when placed in tension.

In certain applications the use of a poly-based laminate film has also been successful. For example, the inner container can be made from a laminate while the outer container may be made from a standard polyethylene material.

Both the inner and the outer containers 12 and 112 can be adapted to contain liquid 14. In the present embodiment the liquid or solution is placed in the inner container. The inner container is the same shape as the outer container but the inner container is smaller thus fitting inside the outer container. Nothing is contained inside the outer container in this embodiment except air.

An effective salt solution for use in the heat pack 10 has been found to be an aqueous solution of sodium acetate trihydrate. While solution strength can range, a mixture of 100 g water and approximately 50–100 g sodium acetate has proven effective.

One mixture involved 75 g of sodium acetate trihydrate to 100 g of water. The solution was heated to between 170–190° F. and then super-cooled. The solution was then placed in the inner container which is hermetically sealed along all 4 edges.

This particular solution (and others in the ranges indicated) has been found desirable as it can be easily triggered to provide heat having a substantially constant temperature. If the super-cooled solution has been heated to a high enough temperature above its melting point before being cooled, it will also remain stable in its super-cooled state even when cooled to temperatures below its melting point. The super-cooled solution will maintain this state until triggered by mixture with air from the outer container.

To trigger the pack the user applies firm but reasonable pressure in a squeezing motion to the exterior of the pack.

Figure 7:
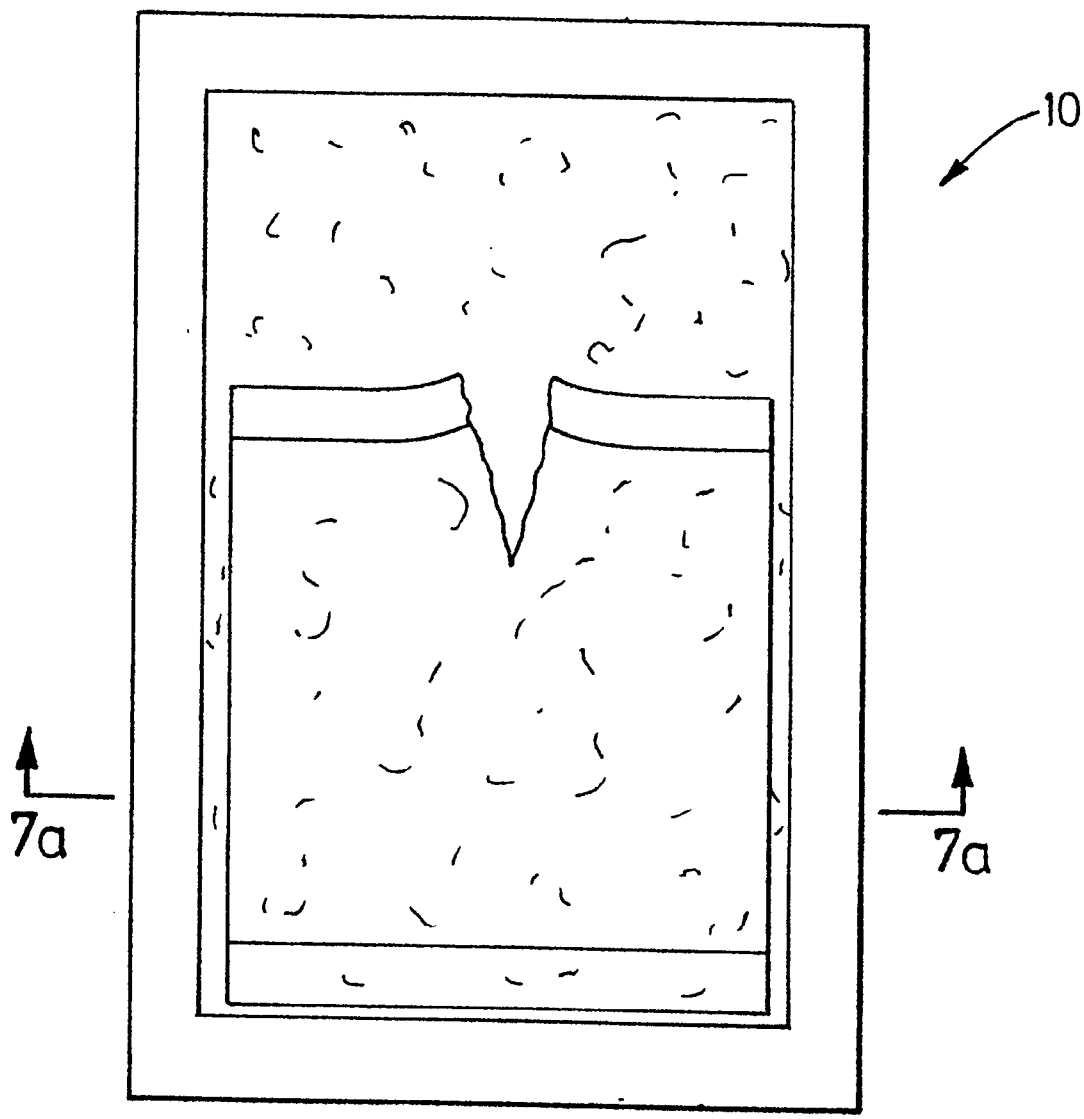
FIG. 7 is a top view of the same embodiment of the present invention showing the pack after activation.
Figure 7A:
FIG. 7A is a sectional view along line 7A—7A of FIG. 7.

As solution 14 is generally an incompressible liquid such as water, the resultant force tends to force the solution out of the inner container 12 by rupturing one or more of the seams on the edges of the inner container 20, thereby allowing the solution 14 and the air from the outer container to mix. This is sufficient to reliably trigger the crystallization of the super-cooled solution, thereby releasing the latent heat of fusion. The pack 10 is thus warmed and can be applied to the user. This rupturing of the inner container is shown in FIG. 7.

The sheet material can be chosen and manipulated so that the force required to rupture the inner container can be easily achieved with one hand. Due to the fluid nature of the pack however, it is highly improbable that any force accidentally applied would trigger the pack. If desired the inner container 12 may further he secured to the outer container 112 at one seam by heat sealing all four sheets of material together for a distance along one edge. This may facilitate optimal force distribution when the pack is squeezed externally allowing the rupture to occur in the must efficient manner.

Figure 8:
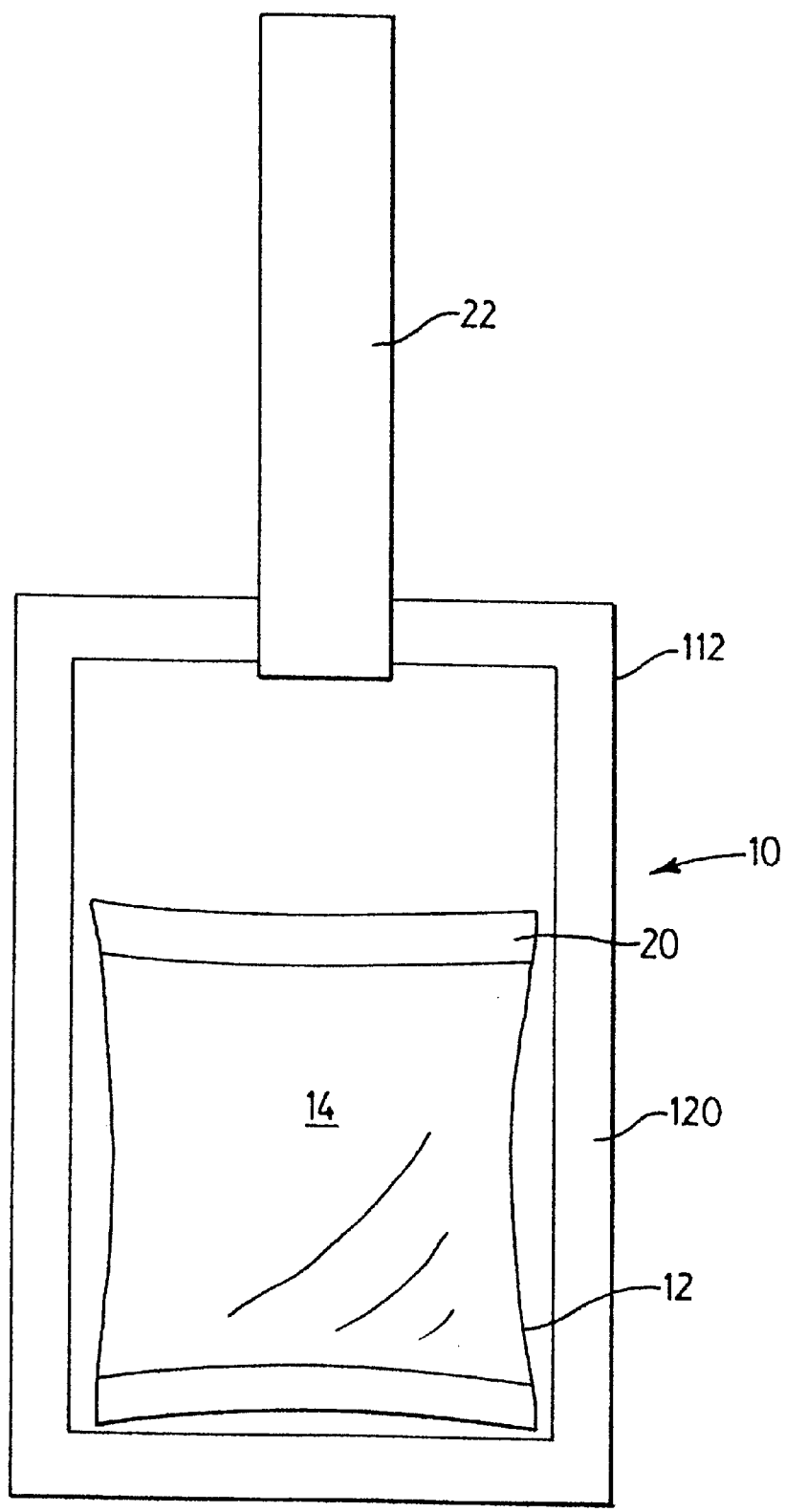
FIG. 8 is a top view of the same embodiment of the present invention in the inactivated state additionally showing an optional securing means.

Use of sodium acetate trihydrate in solution is one chemical that has proven effective. Other chemicals however with suitable characteristics could be used. One aspect that is required is a stable and relatively rapid phase change once crystallization initiates. A number of applications require that the temperature of the phase change suit warming of human skin. Referring to FIG. 8, optionally an adhesion strip or other securing means 22 may be affixed to the pack to assist with retaining the pack in contact with a person to effect warming.

The latent heat of fusion the solution used in the preferred embodiment reliably heats a pack 10 to within a narrow range of about 103–106° F., most often near 105° F. The phase change, and thus heating, occurs in a few seconds, and the heat is retained for several minutes. With gentle kneading the heat distributes evenly.

As stated, other chemicals with different properties and particular different temperatures of phase change may also be used. For certain applications much higher temperatures might be desirable which would require the use of chemicals having higher heats of latent fusion. Heat packs generally could be used for heating a number of things in addition to humans, including other liquids, foods, etc. Some of these applications could require that the heat pack develop temperatures of 130–150° F. or higher.

If greater consistency is desired in the crystallized solution, say for larger packs, a viscosity enhancing agent or gelling agent may be added to the solution. One such agent that has proven effective is hydroxy ethyl cellulose polymer.

It will be appreciated that the above description related to one preferred embodiment by way of example only. In particular, other embodiments include a one container baffled system with at least two separate compartments, and a second embodiment of the dual container system wherein the solution is housed in the outer container and the air is housed in the inner, rupturable container. Variations in the shape and configuration of the heat pack for different applications are also within the scope of this invention. Many other variations on the invention will be obvious to those knowledgeable in the field, and such obvious variations are within the scope of the invention as described, whether or not expressly described.

What is claimed is:

1. A heat pack comprising;
    a container including a first layer of flexible sheet material and a second layer of flexible material, means for bonding said layers together to form laminated sheet material, means for creating first and second compartments within said container, wherein one of said first and second compartments houses a super-cooled aqueous solution and the other of said first and second compartments is empty, and a rupturable seal between said first and second compartments.

2. A heat pack according to claim 1 wherein said super-cooled aqueous solution is a salt solution.

3. A heat pack according to claim 2 wherein said salt solution is a sodium acetate trihydrate solution.

4. A heat pack according to claim 3 wherein said salt solution has a latent heat of fusion within a range of approximately 103–106° F.

5. A heat pack according to claim 4 wherein said salt solution has a latent heat of fusion of approximately 105° F.

6. A heat pack according to claim 1 wherein said means for creating first and second compartments comprises a separate inner container disposed in the heat pack.

7. A heat pack according to claim 1 wherein said means for creating first and second compartments comprises a flangible seal separating the container into two distinct sealed compartments.

* * * * *